(12) United States Patent  
Takeda et al.

(10) Patent No.: US 8,998,805 B2  
(45) Date of Patent: Apr. 7, 2015

(54) LARYNGOSCOPE

(75) Inventors: Yoshimasa Takeda, Okayama (JP); Kiyoshi Morita, Okayama (JP); Takeharu Kobayashi, Izumi (JP)

(73) Assignee: National University Corporation Okayama University, Okayama (JP)

( * ) Notice: Subject to any disclaimer, the term of this patent is extended or adjusted under 35 U.S.C. 154(b) by 432 days.

(21) Appl. No.: 13/395,052

(22) PCT Filed: Aug. 19, 2010

(86) PCT No.: PCT/JP2010/064008  
§ 371 (c)(1),  
(2), (4) Date: Mar. 8, 2012

(87) PCT Pub. No.: WO2011/030654  
PCT Pub. Date: Mar. 17, 2011

(65) Prior Publication Data  
US 2012/0178999 A1 Jul. 12, 2012

(30) Foreign Application Priority Data  
Sep. 8, 2009 (JP) ................................. 2009-207006

(51) Int. Cl.  
*A61B 1/267* (2006.01)  
*A61B 1/00* (2006.01)  
*A61M 16/04* (2006.01)

(52) U.S. Cl.  
CPC ............. *A61B 1/267* (2013.01); *A61B 1/00087* (2013.01); *A61B 1/00131* (2013.01); *A61M 16/0488* (2013.01)

(58) Field of Classification Search  
None  
See application file for complete search history.

(56) References Cited

U.S. PATENT DOCUMENTS

| 4,114,609 | A | | 9/1978 | Moses | |
|---|---|---|---|---|---|
| 4,579,108 | A | * | 4/1986 | Bauman | 600/186 |
| 6,855,108 | B2 | * | 2/2005 | Ishibiki et al. | 600/127 |
| 7,471,984 | B2 | * | 12/2008 | Sakagami et al. | 607/48 |
| 7,695,430 | B2 | * | 4/2010 | Axelgaard | 600/142 |
| 7,695,433 | B2 | * | 4/2010 | Simons | 600/186 |
| 2005/0059863 | A1 | * | 3/2005 | Zilch | 600/188 |
| 2005/0187434 | A1 | | 8/2005 | Dey et al. | |
| 2010/0249639 | A1 | * | 9/2010 | Bhatt | 600/546 |

FOREIGN PATENT DOCUMENTS

| JP | 2005-319245 | 11/2005 |
|---|---|---|
| JP | 2006-326111 | 12/2006 |
| JP | 2008-289667 | 12/2008 |
| JP | 2009-039552 | 2/2009 |

* cited by examiner

*Primary Examiner* — Christian Sevilla  
*Assistant Examiner* — Eric S Gibson  
(74) *Attorney, Agent, or Firm* — Jordan and Hamburg LLP

(57) ABSTRACT

A laryngoscope is provided with which an operator can directly observe the trachea inlet portion of a patient easily by safely and surely lifting the epiglottis of the patient with a proximal end portion of a laryngoscope blade which is inserted in the mouth of the patient. The blade is connected to a distal end portion of a grippable handle, a first electrode is mounted on a distal end portion of the blade, and a second electrode is configured to adhere to a skin surface of the patient in the vicinity of the epiglottis, and a low frequency current is supplied to flow between the first electrode and the second electrode.

5 Claims, 8 Drawing Sheets

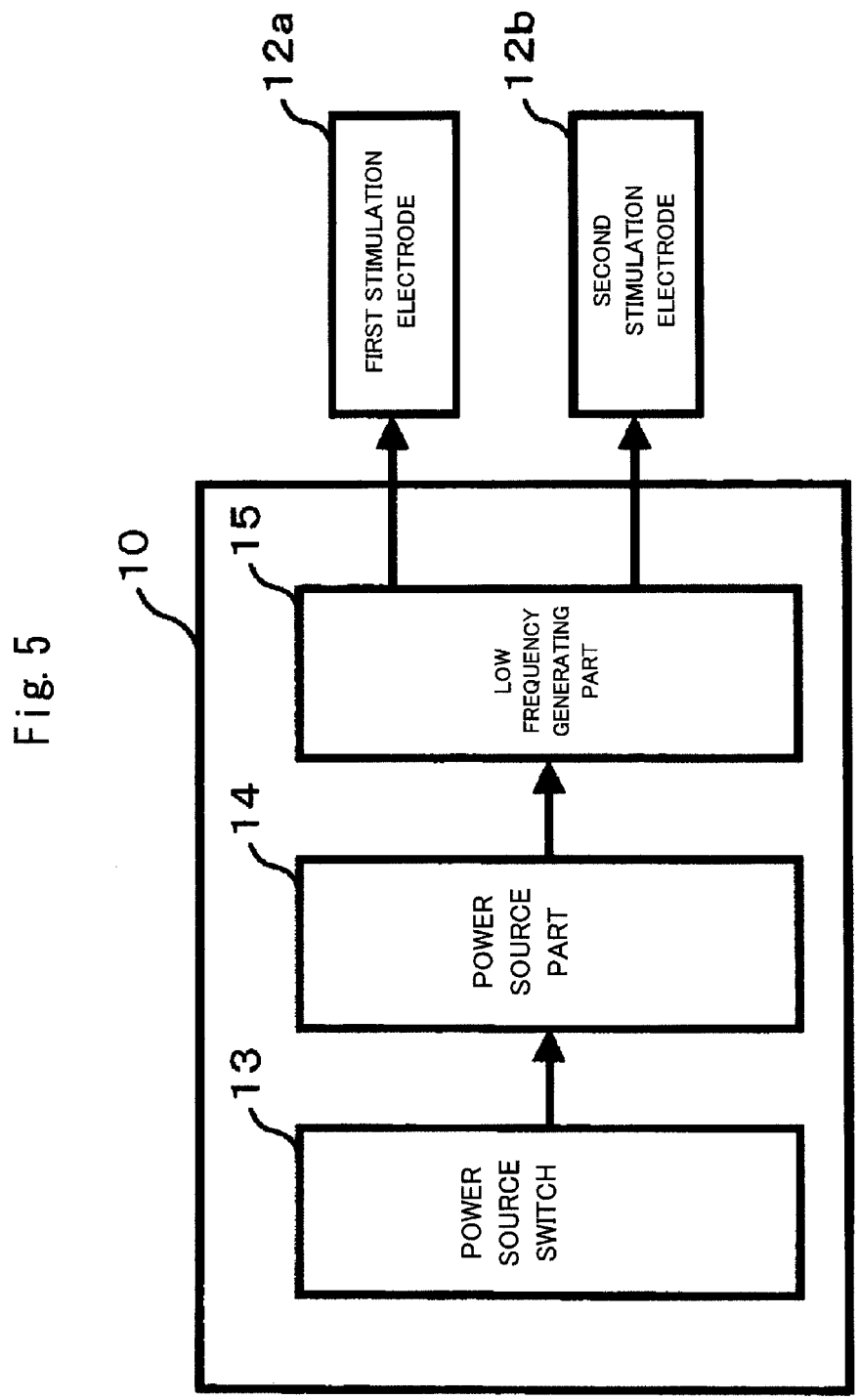

LARYNGOSCOPE

BACKGROUND OF THE INVENTION

The present invention relates to a laryngoscope, and more particularly to a laryngoscope which is used for enabling an operator to visually recognize a trachea inlet portion by lifting an epiglottis which is used in fields of anesthesia, emergency, an intensive care and the like.

In fields of anesthesia, emergency, an intensive care field and the like, it has been practiced in general that a tube is inserted into a trachea from an oral cavity thus ensuring the clearing of an airway which is a passage of oxygen necessary for respiration (airway control).

In carrying out the airway control, prior to the insertion of the tube, the treatment referred to as laryngeal exposure is carried out for enabling an operator to visually recognize a trachea inlet portion. That is, a lid portion referred to as an epiglottis is present in the trachea inlet portion and this epiglottis prevents food or drink from entering a trachea. In carrying out the airway control, when the epiglottis is not lifted, there may be a case where a field of view of the operator is obstructed so that the operator cannot visually recognize the trachea inlet portion. To cope with such a circumstance, laryngeal exposure is carried out so as to allow the operator to visually recognize the trachea inlet portion by lifting the epiglottis.

In the laryngeal exposure, instrument referred to as a laryngoscope having a blade which is insertable into a mouth of a patient is used. To be more specific, the laryngeal exposure is the treatment where a tongue portion is pushed sideward by the blade of the laryngoscope, and an epiglottis is lifted by pushing a proximal end portion of the epiglottis with a distal end portion of the blade.

Conventionally, the airway control is carried out by a doctor. When the epiglottis is not lifted so that the doctor cannot sufficiently visually recognize an airway inlet portion, he carries out the airway control by estimating a trachea inlet portion based on his technique and hunch.

To cope with such a situation, there has been proposed a McCoy laryngoscope as a laryngoscope with which an epiglottis can be easily lifted (see JP-A-2005-319245, for example). The McCoy laryngoscope has the structure by which a force can be easily applied to a root portion of the epiglottis, that is, the structure where a distal end of a blade of the laryngoscope is arranged by way of a hinge, and a lever for bending the distal end of the blade is arranged on a handle. In this McCoy laryngoscope, in response to the manipulation of the lever, the distal end of the blade is bent thus pushing a proximal end portion of the epiglottis so that the epiglottis can be lifted mechanically.

SUMMARY OF THE INVENTION

However, in the McCoy laryngoscope, the epiglottis is mechanically lifted as described above. Accordingly, when tracheal intubation (insertion of a tube into a trachea from an oral cavity) is carried out in an emergency case such as stopping of respiration of a patient, an excessively large force is applied to the lever due to a tension of a doctor so that there may be a case where blood bleeds from a root portion of the epiglottis or the root portion swells when the excessively large force is applied resulting in a critical situation. Accordingly, situations where the McCoy laryngoscope can be used are limited.

Recently, tracheal intubation is admitted also to emergency life guards besides doctors. Accordingly, also in a case where the tracheal intubation is carried out by an emergency life guard, the emergency life guard is required to directly observe the trachea inlet portion to carry out the reliable tracheal intubation.

As instrument useful in tracheal intubation besides a tracheal intubation tube, there has been also proposed a laryngoscope which incorporates a CCD camera and an LCD monitor therein, for example. However, in this laryngoscope, the tracheal intubation is carried out while checking the inside of an oral cavity on a screen of the LCD monitor so that an operator cannot directly observe a trachea inlet portion. Accordingly, the use of this laryngoscope is not admitted to the emergency life guard.

The present invention has been made under such circumstances, and it is an object of the present invention to provide a laryngoscope by which an operator can directly observe a trachea inlet portion easily by safely and surely lifting the epiglottis.

To achieve the above-mentioned object, the invention is directed to a laryngoscope where a proximal end of a blade which is inserted from a mouth of a patient and lifts an epiglottis for enabling an operator to visually recognize a trachea inlet portion is connected to a distal end of a grippable handle, wherein a first electrode is mounted on a distal end portion of the blade, and a second electrode is arranged in the vicinity of the epiglottis in a state where the second electrode is capable of coming into contact with a part of a human body whereby a low frequency current flows between the first electrode and the second electrode.

Further, for the laryngoscope of the invention the low frequency current may be a pulse current having a frequency of 10 to 100 Hz and an electric current value of 10 mA to 100 mA.

The first electrode of the laryngoscope of the invention may be arranged on the distal end portion of the blade by way of an insulating cover which covers at least the distal end portion of the blade.

The second electrode of the laryngoscope of the invention may be configured to adhere to a skin surface in the vicinity of the epiglottis.

In the laryngoscope of the invention, an imaging part may be mounted on the distal end portion of the blade, a display part tiltably mounted on a proximal end of the handle, and an image picked up by the imaging part displayed on the display part.

ADVANTAGE OF THE INVENTION

In the laryngoscope of the invention, which includes the first electrode and the second electrode, a low frequency current flows between the first electrode and the second electrode so that muscles around an epiglottis are shrunken by stimulation due to this low frequency current thus lifting the epiglottis. Accordingly, an operator can carry out the tracheal intubation surely. Further, also in a case where a life guard cannot carry out the tracheal intubation (a case where the life guard cannot visually recognize the trachea) conventionally, the life guard can carry out the tracheal intubation so that lives of many patients can be saved.

When a pulse current having a frequency of 10 to 100 Hz and an electric current value of 10 mA to 100 mA is used as the low frequency current, the laryngeal exposure can be carried out without imposing an excessive burden on a patient.

When the first electrode is arranged on the distal end portion of the blade by way of an insulating cover which covers at least the distal end portion of the blade, the electrode can be arranged on the distal end portion of the blade regardless of the material of the blade. Accordingly, the laryngeal exposure using a low frequency current can be carried out using any kind of blade.

By adhering the second electrode to the skin surface in the vicinity of an epiglottis of a patient and by allowing a low frequency current to flow between the first electrode and the second electrode, it is possible to shrink muscles around the epiglottis by such a low frequency current so that the epiglottis can be lifted.

When an imaging part is mounted on the distal end portion of the blade, a display part is tiltably mounted on a proximal end of the handle, and an image picked up by the imaging part is displayed on the display part, in carrying out the tracheal intubation, an operator can visually recognize a trachea inlet portion of a patient based on the image displayed on the display part. Accordingly, the operator can visually recognize the trachea inlet portion in a relaxed posture and hence, the operator can easily carry out the tracheal intubation.

BRIEF DESCRIPTION OF THE DRAWINGS

FIG. 5 is a block diagram showing the electrical constitution of the laryngoscope according to the embodiment.

DETAILED DESCRIPTION OF THE INVENTION

Hereinafter, the mode for carrying out the present invention (hereinafter referred to as "embodiment") is explained.

Figure 1:
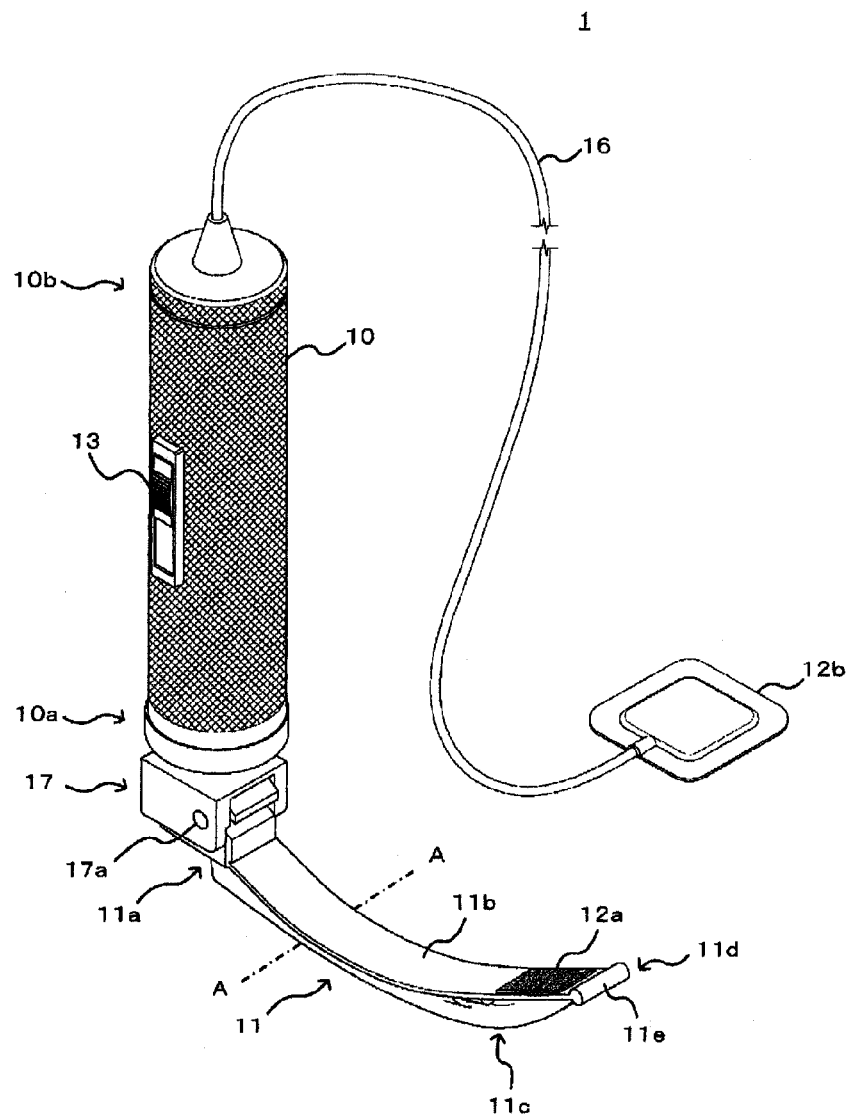
FIG. 1 is a view showing the schematic constitution of a laryngoscope according to an embodiment of the present invention.
Figure 2:
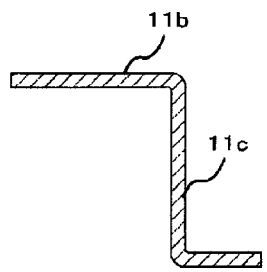
FIG. 2 is a cross-sectional view taken along a line A-A in FIG. 1.

FIG. 1 is a perspective view showing the external appearance of a laryngoscope according to the embodiment, and FIG. 2 is a cross-sectional view taken along a line A-A in FIG. 1. As shown in FIG. 1, the laryngoscope 1 includes a handle 10 and a blade 11 which is mounted on the handle 10. On a contact surface formed on a distal end of the blade 11 which is brought into contact with a proximal end portion of an epiglottis, a first electrode 12a is mounted. As a constitutional element provided separate from a body of the laryngoscope 1, a second electrode 12b is arranged at a position where the second electrode 12b becomes electrically conductive with the first electrode 12a. A power source switch 13 is arranged on an outer peripheral surface of the handle 10, and a power source part 14 and a low frequency generating part 15 are arranged in the inside of the handle 10.

To allow a person who carries out the airway control for a patient such as a doctor or an emergency life guard (hereinafter referred to as "operator") to easily manipulate the blade 11 when the operator grips the handle 10, the handle 10 is formed into an approximately cylindrical shape with a diameter which allows the operator to easily grip the handle 10, and also knurling is formed on a surface of the handle 10 in the longitudinal, lateral and oblique directions.

A connection case 17 is formed on a distal end portion 10a of the handle 10, a shaft 17a is mounted in the inside of the case 17 in a traversing manner, and, in the inside of the case 17, a proximal end portion 11a of the blade 11 is pivotally supported on the shaft 17a in a foldable manner.

The blade 11 is a portion which is inserted into a larynx through a mouth of the patient. As shown in FIG. 2, the blade 11 is formed into an approximately rectangular plate shape, and has a tongue depressor 11b which is bent downwardly in a concave shape. A rectangular pushing plate 11c for pushing a tongue toward one side in an oral cavity of the patient is formed on a side edge of the tongue depressor 11b in a downwardly extending manner. A contact protrusion 11e having a circular rod shape is formed on a distal end portion 11d of the tongue depressor 11b in a projecting manner thus decreasing a contact pressure applied to skin tissue in the vicinity of an epiglottis in the oral cavity. Further, the blade 11 is made of a material having rigidity such as metal or a synthetic resin, for example.

The first electrode 12a is, as described above, arranged on the distal end portion 11d of the tongue depressor 11b, and is formed such that the first electrode 12a can be brought into contact with a contact surface of a proximal end portion of the epiglottis of the patient. Further, the first electrode 12a is electrically connected to a low frequency generating part 15 via a wire not shown in the drawing which is embedded in the blade 11.

Figure 3:
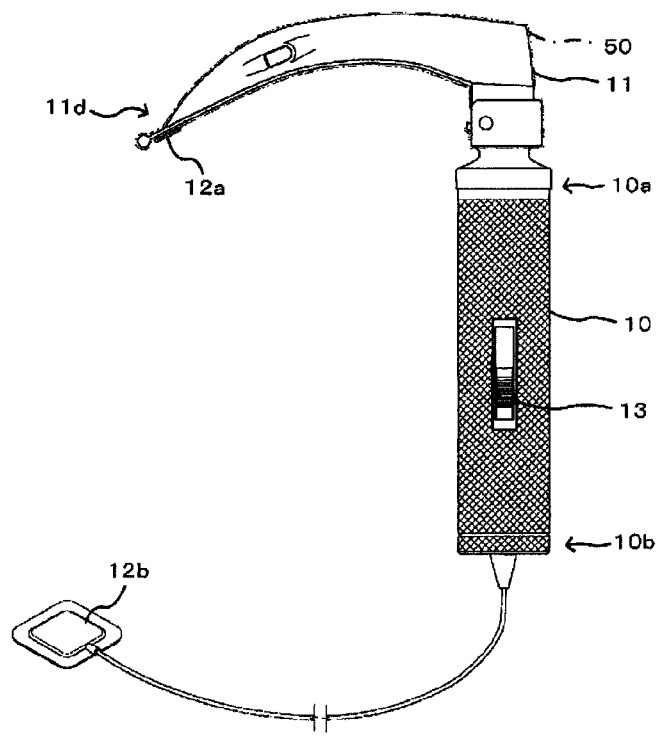
FIG. 3 is view showing a modification of the laryngoscope.

As shown in FIG. 3, a surface of the blade 11 may be covered with an insulating cover 50 and the first electrode 12a may be arranged on the distal end portion 11d of the blade 11 by way of the cover 50. In this case, the wire is formed on the surface of the cover 50 and the first electrode 12a and the low frequency generating part 15 are electrically connected to each other via the wire. Accordingly, even with the use of a blade having a distal end portion 11d where an electrode is not arranged, it is possible to carry out laryngeal exposure using a low frequency current.

Further, it is desirable to form the cover 50 using a material which has the insulation property as described above and also has flexibility, for example, using a silicon resin or the like. This is because the cover 50 is used for blades having different shapes.

The second electrode 12b is configured such that the second electrode 12b is embedded in a pad having an adhesive property on a surface thereof (not shown in the drawing), and can adhere to a skin surface of the patient in the vicinity of the epiglottis. The second electrode 12b is connected to a proximal end portion 10b of the handle 10 via a wire 16, and is electrically connected to the low frequency generating part 15 arranged in the inside of the handle 10. The position where the second electrode 12b is connected is not limited to the proximal end portion 10b of the handle 10 and, for example, the second electrode 12b may be connected to an external power source device not shown in the drawing, and a low frequency current may be supplied to the second electrode 12b from the power source device.

Figure 4A:
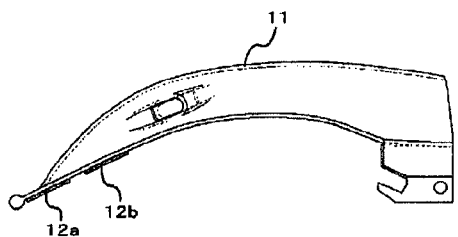
FIGS. 4A and 4B are views showing another modification of the laryngoscope.
Figure 4B:
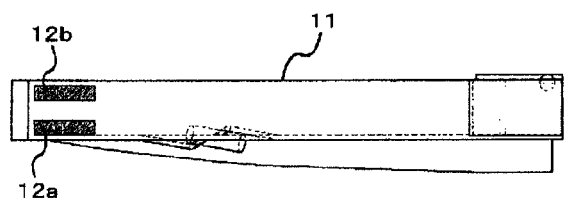

The second electrode 12b may also be arranged at the distal end portion 11d of the blade 11 together with the first electrode 12a. For example, as shown in FIG. 4A, the first electrode 12a and the second electrode 12b may be arranged at the distal end portion 11d along the direction equal to the direction along which the blade 11 extends with a predetermined distance therebetween or. Alternatively, as shown in FIG. 4B, the first electrode 12a and the second electrode 12b may be arranged along the direction orthogonal to the direction along which the blade 11 extends with a predetermined distance therebetween. In this manner, by arranging the first electrode 12a and the second electrode 12b on the distal end portion 11d of the blade 11, it is possible to make the laryngoscope 1 compact. Further, in carrying out the laryngeal exposure, in the same manner as the laryngoscope 1 described above, it is possible to allow a low frequency current to flow between the first electrode 12a and the second electrode 12b through muscles around the epiglottis of the patient so that it is possible to give electric stimulation to the muscles. Accordingly, the operability of the laryngoscope 1 in carrying out the laryngeal exposure is further enhanced.

Here, although the example where the first electrode 12a is arranged on the distal end portion 11d of the blade 11 by way of the cover 50 has been explained heretofore, the second electrode 12b may be arranged on the distal end portion 11d of the blade 11 by way of the cover 50 in the same manner.

The power source switch 13 is a slide type switch, for example, and turns on/off the supply of power source from the power source part 14. Here, the power source switch 13 is not limited to the slide type switch, and a rotary switch or a push switch is also used as the power source switch 13, for example.

The power source part 14 is a part for supplying electric power to the low frequency generating part 15. As the power source part 14, a charging nickel hydrogen battery or a charging lithium battery may be used, for example.

The low frequency generating part 15 is a circuit which generates a low frequency current, and supplies the low frequency current to the first electrode 12a and the second electrode 12b. The low frequency current generated in the low frequency generating part 15 gives tetanic stimulation (high-frequency repetitive stimulation) having a frequency of 50 Hz and an electric current value of 50 mA, for example, to a patient.

The low frequency generating part 15 is constituted of a digital signal generating circuit, a DA conversion circuit and a filter (none of these parts shown), for example. The digital signal generating circuit is a circuit having a function of storing waveform data for defining a waveform of a low frequency current and a function of outputting a digital signal in accordance with the waveform data. The digital signal generating circuit stores plural kinds of waveform data, and can change a waveform of an output corresponding to the frequency. Further, the DA conversion circuit is a circuit having a function of outputting a source waveform by performing the analogue conversion of a digital signal outputted from the digital signal generating circuit. Further, the filter is a filter for performing antialiasing of the source waveform, and a low-pass filter is typically used as the filter.

Next, the electrical constitution of the laryngoscope 1 is explained. FIG. 5 is a block diagram showing the electrical constitution of the laryngoscope according to this embodiment.

As shown in FIG. 5, in the inside of the handle 10 of the laryngoscope 1, the low frequency generating part 15 is connected to the power source switch 13 via the power source part 14. The low frequency generating part 15 is also connected to the first electrode 12a and the second electrode 12b which are arranged as parts separate from the handle 10.

In the laryngoscope 1 having such an electrical constitution, when the power source switch 13 is turned on, a control signal is transmitted to the power source part 14 during a period where the power source switch 13 is in an ON state. During a period where the power source part 14 receives the control signal, the power source part 14 supplies an electric current (constant current, for example) to the low frequency generating part 15. When the electric current is supplied to the low frequency generating part 15, the low frequency generating part 15 converts the supplied electric current into a pulse having a predetermined frequency and an electric current value thus generating a low frequency current, and supplies the generated low frequency current to the first electrode 12a and the second electrode 12b. In this manner, in the laryngoscope 1, during a period where the power source switch 13 is in an ON state, a low frequency current flows between the first electrode 12a and the second electrode 12b. Here, the predetermined frequency and the predetermined electric current value are a frequency of 50 Hz and an electric current value of 50 mA, for example, respectively.

Figure 6:
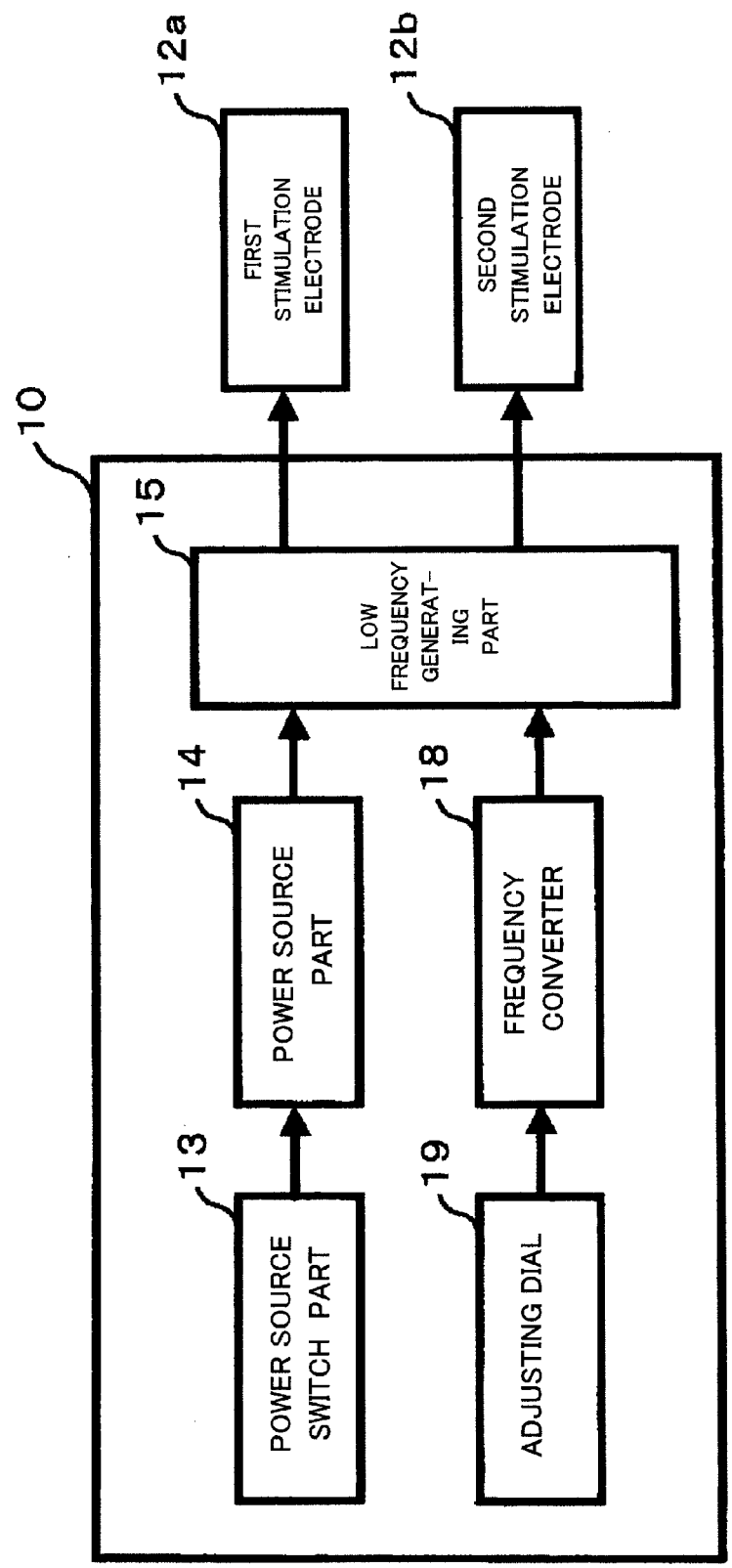
FIG. 6 is a view showing another modification of the laryngoscope.

Here, as shown in FIG. 6, in the inside of the handle 10, in addition to the power source part 14 and the low frequency generating part 15, a frequency converter 18 and an adjusting dial 19 may be arranged for changing a frequency and an electric current value of the generated low frequency current in stages. The adjusting dial 19 is configured such that a channel to be used can be selected from channels to which a plurality of frequencies and electric current values are allocated in stages, for example. Further, the frequency converter 18 stores data on a plurality of low frequency currents which differ in frequency and electric current value, and transmits a current setting signal corresponding to the channel selected by the adjusting dial 19 to the low frequency generating part 15.

The frequency converter 18 is an electronic volume for adjusting a frequency and an electric current value of the low frequency current which the low frequency generating part 15 generates, and the low frequency generating part 15 generates a low frequency current having the frequency and the electric current value which are adjusted by the frequency converter 18.

In the laryngoscope 1 having such a constitution, when the channel to be used is selectively manipulated using the adjusting dial 19, a control signal is transmitted to the frequency converter 18 from the adjusting dial 19. When the frequency converter 18 receives the control signal, the frequency converter 18 transmits an electric current setting signal corresponding to the control signal to the low frequency generating part 15. The low frequency generating part 15 generates a low frequency current corresponding to the electric current setting signal, and supplies the generated low frequency current to the first electrode 12a and the second electrode 12b.

Further, the laryngoscope 1 where the frequency converter 18 and the adjusting dial 19 are arranged can generate a low frequency current having a desired frequency and electric current value in accordance with the definition of the waveform data. For example, the low frequency current which the laryngoscope 1 can generate is not limited to the above-mentioned low frequency current having the frequency of 50 Hz and the electric current value of 50 mA. That is, the laryngoscope 1 can also generate a low frequency current having a frequency which is changed in stages or having an electric current value which is changed in stages.

In this manner, according to the laryngoscope 1 having such a constitution, it is possible to selectively generate a low frequency current having a frequency and an electric current value which are allocated to the channel. Accordingly, in carrying out the laryngeal exposure, it is possible to select a low frequency current having a frequency and an electric current value corresponding to an age, physical strength or the like of a patient so that it is possible to carry out the laryngeal exposure without imposing an excessively large burden on the patient.

A range of frequency allocated to the channels is 10 to 100 Hz, and a range of the electric current value allocated to the channels is 10 mA to 100 mA, for example. The frequency is allocated for every 10 Hz in stages, and the electric current value is allocated for every 10 mA in stages, for example.

Next, a method of carrying out an airway control using the laryngoscope 1 is explained. In this embodiment, a method of carrying out an airway control using tracheal intubation is explained. The tracheal intubation is a method of carrying out an airway control by inserting a tracheal intubation tube 20 into a trachea from a mouth or a nose by way of a larynx. Firstly, the tracheal intubation tube 20 and a stilet 30 which are used in the tracheal intubation are simply explained.

Figure 7A:
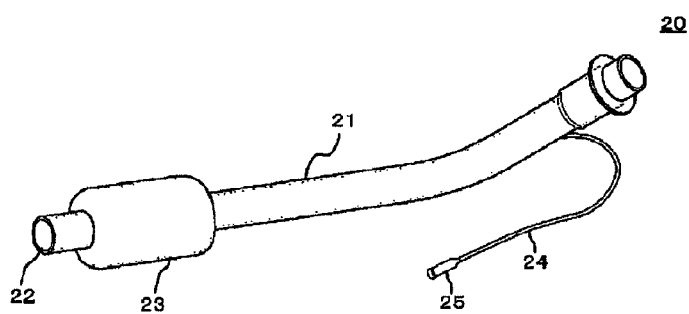
FIGS. 7A and 7B are views showing a tracheal intubation tube.

In the tracheal intubation tube 20, as shown in FIG. 7A, an opening portion 22 is formed at a distal end of an airway tube 21 through which air passes, and a cuff portion 23 is formed at a position slightly behind the opening portion 22 in a state where the cuff portion 23 surrounds the airway tube 21. The cuff portion 23 is formed in an expansible and shrinkable manner, and a distal end of an inflating tube 24 is connected to the cuff portion 23. Further, an inflating valve 25 for injecting fluid such as air is mounted on a proximal end portion of the inflating tube 24. This tracheal intubation tube 20 is characterized in that a length of the distal end portion of the tracheal intubation tube 20 (a length from the opening portion 22 to the cuff portion 23) is set smaller than a length of a corresponding portion of a usual tracheal intubation tube, and the opening portion 22 is cut so as to form a flat opening.

Figure 7B:
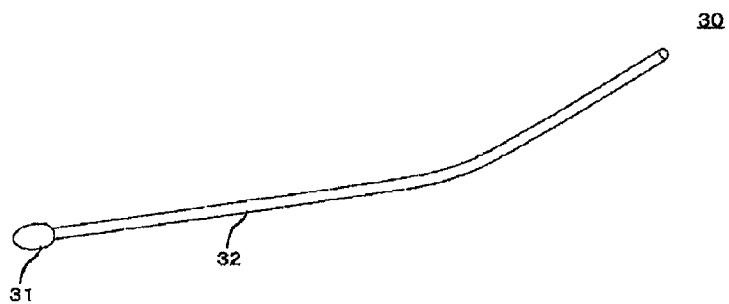

As shown in FIG. 7B, the stilet 30 includes a streamline-shaped guide portion 31 at a distal end thereof. A rod 32 is connected to the guide portion 31. The rod 32 is formed of a metal pipe having an outer diameter smaller than an inner diameter of the tracheal intubation tube 20. The rod 32 has the degree of rigidity that an operator can easily bend the rod 32 with his hand and the rod 32 can maintain a bent state. Further, the guide portion 31 has a streamlined shape so that even when the stilet 30 projects from the opening portion 22 of the tracheal intubation tube 20, the stilet 30 can be easily retracted to the inside of the tracheal intubation tube 20.

Figure 8:
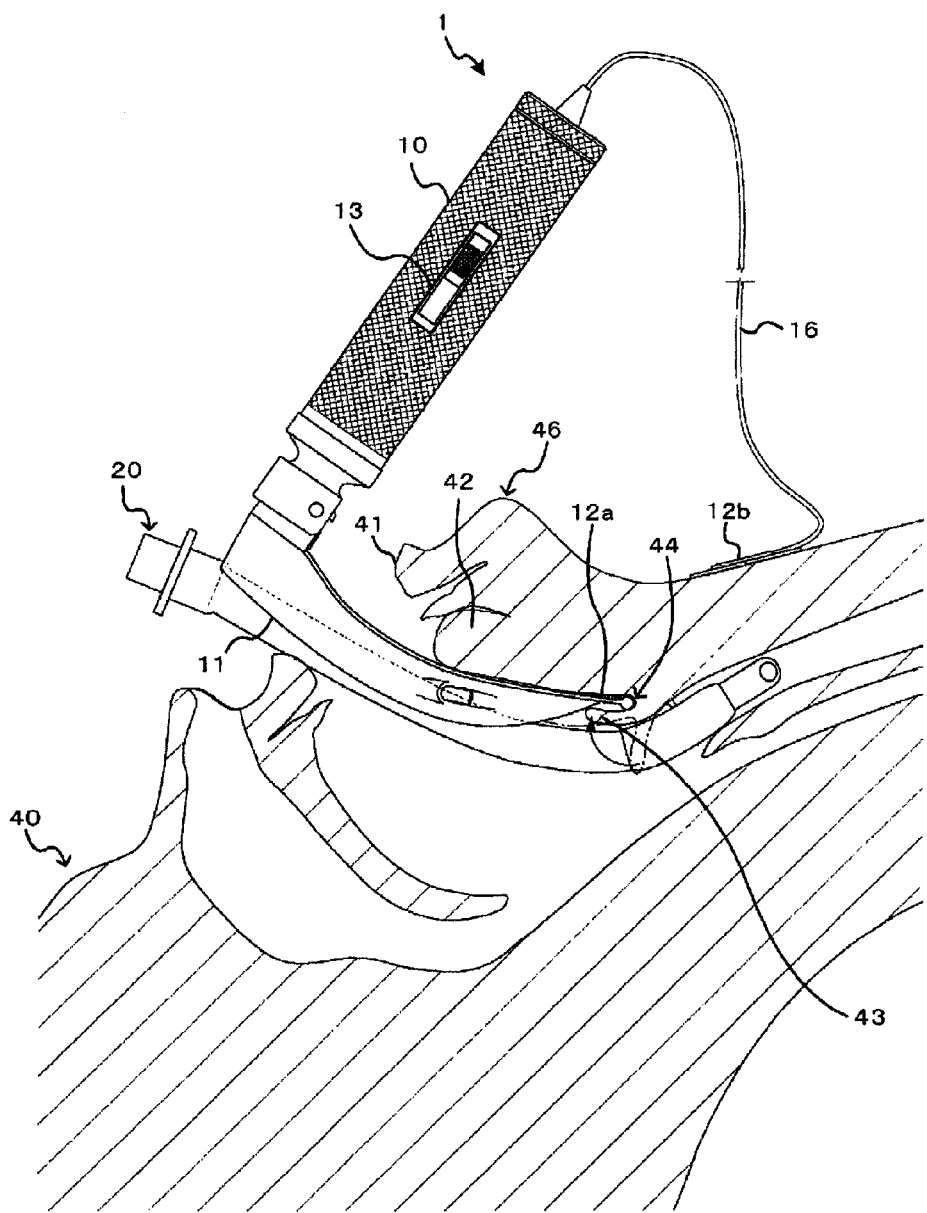
FIG. 8 is a view showing a use state of the laryngoscope according to the embodiment.

Using the laryngoscope 1, the tracheal intubation tube 20 and the stilet 30 having the above-mentioned constitution, it is possible to carry out the tracheal intubation shown in FIG. 8. Firstly, a lower jaw 46 of a patient 40 is lifted in a state where the patient 40 lies on his back.

Figure 9A:
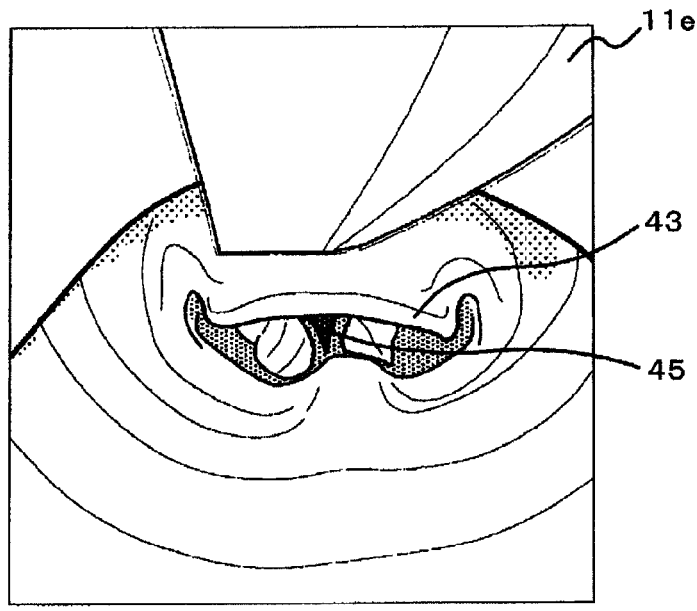
FIGS. 9A and 9B are views showing the manner how an epiglottis changes.

Next, the blade 11 of the laryngoscope 1 is inserted through lips 41 of the patient 40, and a tongue portion 42 is pushed sideward (leftward as viewed from the operator, for example) and, thereafter, the first electrode 12a is brought into contact with the contact surface of the proximal end portion 44 of the epiglottis 43. At this stage, the epiglottis 43 of the patient 40 falls downward as indicated by a broken line in the drawing thus taking a state where the epiglottis 43 closes a trachea inlet portion 45 (see FIG. 9A). Then, the second electrode 12b is made to adhere to a part of the patient at a position where a low frequency current can flow between the second electrode 12b and the first electrode 12a (for example, on a skin of the patient between a cartilago thyroidea and an annular cartilage). Although the adhesion of the second electrode 12b is made after the insertion of the laryngoscope 1 in this embodiment, the order of these steps is not limited to this order.

Figure 9B:
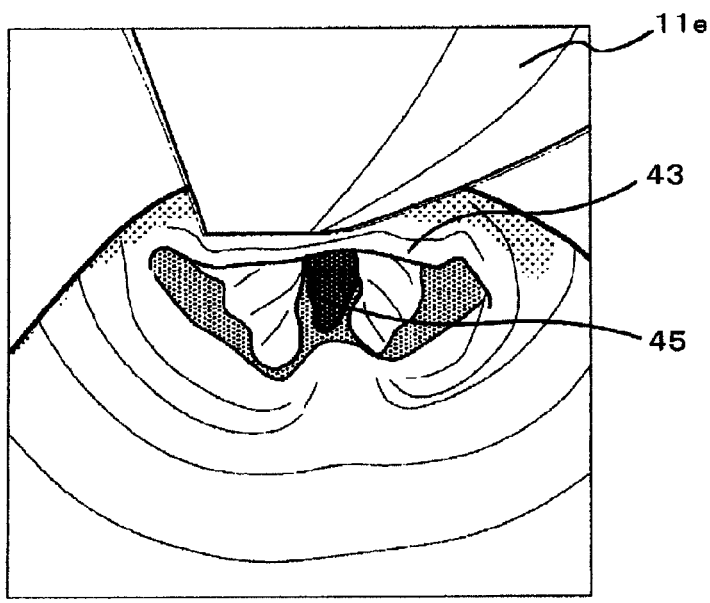

Next, the handle 10 is lifted in the upward direction so that the proximal end portion 44 of the epiglottis 43 is pushed by the distal end portion 11d of the blade 11, and the power source switch 13 is turned on thus allowing a low frequency current to flow between the first electrode 12a and the second electrode 12b. Due to such an operation, electric stimulation is given to muscles around the epiglottis 43 during a period where the power source switch 13 is in an ON state and hence, the muscles are shrunken so that the epiglottis 43 is lifted with time whereby the operator can visually recognize the trachea inlet portion 45 (see FIG. 9B).

The frequency of the low frequency current is set to 50 Hz, and the electric current value of the low frequency current is set to 50 mA. By setting the frequency and the electric current value to such values, it is possible to directly give stimulation to the muscles. When the energy of the low frequency current is low, that is, when the frequency is low and the electric current value is low, the lift of the epiglottis becomes insufficient. On the other hand, when the energy of the low frequency current is high, that is, when the frequency is high and the electric current value is high, inflammation such as burn is caused on the periphery of the epiglottis.

Next, the tracheal intubation tube 20 is inserted into the trachea inlet portion. Such insertion of the tracheal intubation tube 20 is performed in such a manner that a shape of a rod 32 of the stilet 30 is formed in conformity with the trachea of the patient, and the stilet 30 is inserted into the tracheal intubation tube 20 such that the guide portion 31 of the stilet 30 projects from the opening portion 22 of the tracheal intubation tube 20.

As described above, the opening portion 22 of the tracheal intubation tube 20 is cut so as to form a flat opening. Accordingly, when the insertion of the tracheal intubation tube 20 is performed in a state where the stilet 30 is not inserted, the tracheal intubation tube 20 is caught by a larynx chamber which is formed in the trachea inlet portion and hence, the insertion of the tracheal intubation tube 20 cannot be performed well.

Next, the tracheal intubation tube 20 is inserted into the inside of the trachea. After the stilet 30 is pulled out from the tracheal intubation tube 20, the cuff portion 23 is inflated by supplying air into the cuff portion 23 through the inflating valve 25 of the inflating tube 24 thus holding the tracheal intubation tube in place. Here, it is necessary to hold the tracheal intubation tube such that a part of the tracheal intubation tube ranging from the opening portion 22 to the cuff portion 23 is present between the trachea inlet portion and a trachea branch portion which constitutes an end portion of the trachea.

In a conventional tracheal intubation tube, the opening portion 22 is cut obliquely and hence, a length from the opening portion 22 to the cuff portion 23 is long so that it has been difficult to hold the tracheal intubation tube at a proper position in a patient (particularly, a child) whose trachea is short. On the other hand, the opening portion 22 is cut so as to form a flat opening in the tracheal intubation tube 20 and hence, a length from the opening portion 22 to the cuff portion 23 is short and hence, it is possible to easily hold the tracheal intubation tube at a proper position.

As described above, by carrying out the laryngeal exposure using the laryngoscope 1, it is possible to lift the epiglottis 43 due to the electrical stimulation caused by a low frequency current. Accordingly, even in a case where an operator cannot lift the epiglottis 43 by general laryngeal exposure because of lack of high techniques, the operator can lift the epiglottis 43 safely and surely. Accordingly, even a doctor or an emergency life guard having insufficient experience can directly observe the trachea inlet portion so that he can offer the safe medical treatment.

For example, in a case where the laryngeal exposure is carried out using a McCoy laryngoscope described in the prior art, as described above, due to an erroneous operation because of tension or the like, pressure more than necessity is applied to the proximal end portion 44 of the epiglottis 43 thus injuring a proximal portion of the epiglottis in many cases whereby there has been a case where a critical situation is brought about due to hematoma or edema. To the contrary, with the use of the laryngoscope 1, the epiglottis is lifted by electrically shrinking the muscles by applying a preset low frequency current through the switch manipulation and hence, it is possible to prevent the occurrence of hematoma or edema.

Modification

Figure 10:
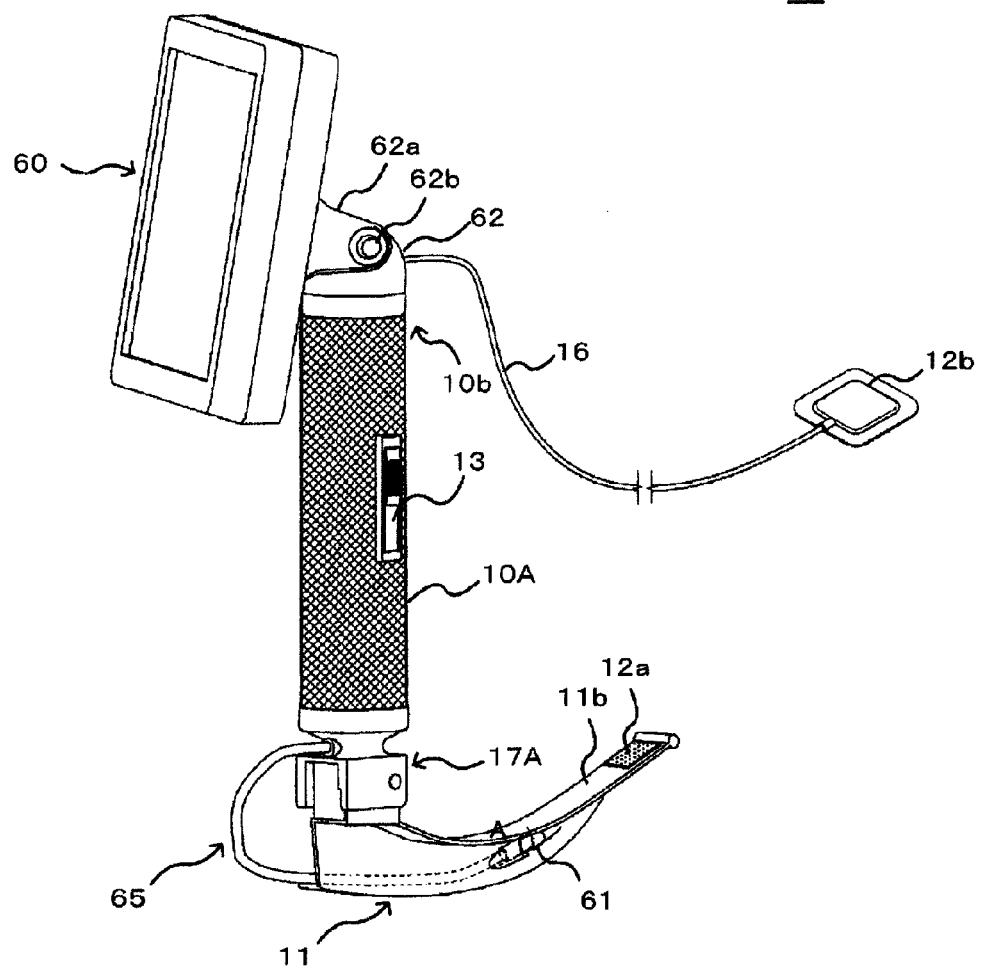
FIG. 10 is a view showing the schematic constitution of a laryngoscope of the modification.

Next, a modification of the laryngoscope 1 according to the embodiment is explained. FIG. 10 is a view showing the schematic constitution of a laryngoscope 1A according to the modification.

The laryngoscope 1A includes an imaging part 61 at a distal end portion of the blade 11, and also includes a display part 60 at the proximal end portion 10b of the handle 10. In carrying out the tracheal intubation, the inside of an oral cavity of a patient is imaged by the imaging part and an image which is imaged by the imaging part 61 is displayed on the display part. Due to such a constitution, an operator can grasp a state in the oral cavity so that the operator can carry out the tracheal intubation more easily. The specific constitution of the laryngoscope 1A is further explained hereinafter.

A blade 11A includes, in addition to the above-mentioned blade 11, a fixing member (not shown in the drawing), and the imaging part 61 is fixed to a surface of a tongue depressor 11b by the fixing member. The fixing member adopts the constitution where the fixing member sandwiches the imaging part 61 from both ends, for example.

The imaging part 61 is formed of a CCD (Charge Coupled Device) camera, for example. A connection terminal is formed on the imaging part 61, and one end of a cable 65 is connected to the imaging part 61 through the connection terminal. An image signal acquired by the imaging part 61 can be outputted to the outside. An illumination part (not shown in the drawing) formed of an LED (Light Emitting Diode) is arranged in the vicinity of the imaging part 61 so that an imaging area where the imaging part 61 can perform imaging can be illuminated.

Although a connection case 17A has the substantially same constitution as the above-mentioned connection case 17, the connection case 17A differs from the connection case 17 with respect to a point that the connection case 17A includes an insertion hole (not shown in the drawing) for inserting a cable 65 into the inside of the connection case 17A. Further, the connection case 17A is configured such that a portion of the cable 65 can be accommodated in the inside of a handle 10A through the insertion hole.

Although the handle 10A has the substantially same constitution as the above-mentioned handle 10, the handle 10A differs from the handle 10 with respect to a point that the handle 10A includes a mounting portion 62 for mounting a display part 60 on a proximal end portion 10b of the handle 10A. The mounting portion 62 includes an arm 62a which extends in the direction opposite to the extending direction of the blade 11, and the arm 62a includes a shaft 62b which extends in the lateral direction at a distal end portion thereof. Further, the display part 60 is pivotally mounted on the handle 10A such that the display part 60 is tiltable with respect to the handle 10A about the shaft 62b.

The display part 60 is formed of an LCD (Liquid Crystal Display), for example. The other end of the cable 65 is connected to the display part 60, the image signal of an image imaged by the imaging part 61 is inputted to the display part 60, and the display part 60 can display the image based on the image signal.

The laryngoscope 1A having such a constitution is used when the laryngeal exposure is carried out in the same manner as the above-mentioned laryngoscope 1. That is, the blade 11 of the laryngoscope 1 is inserted through lips 41 of a patient 40, and a tongue portion 42 is pushed sideward and, thereafter, a first electrode 12a is brought into contact with a contact surface of a proximal end portion 44 of an epiglottis 43. Next, the handle 10 is lifted in the upward direction so that the proximal end portion 44 of the epiglottis 43 is pushed by a distal end portion 11d of the blade 11, and a power source switch 13 is turned on so that the low frequency current flows between the first electrode 12a and a second electrode 12b thus lifting the epiglottis 43.

Subsequently, a tracheal intubation tube 20 is inserted with respect to a trachea inlet portion. The laryngoscope 1A includes an imaging part 61 at the distal end portion of the blade 11, and also includes a display part 60 at a proximal end portion 10b of the handle 10 and hence, the operator can insert the tracheal intubation tube 20 while visually recognizing a state in the trachea inlet portion through an image displayed on the display part 60. Due to such a constitution, an operator can visually recognize the state in the trachea inlet portion easily in a relaxed posture and hence, the operator can easily insert the tracheal intubation tube 20.

Although the present invention has been explained in conjunction with the embodiment and the modification of the embodiment heretofore, the present invention is not limited to the embodiment and various modifications are conceivable.

The invention claimed is:

1. A laryngoscope configured to facilitate observation of a trachea inlet portion of a patient, comprising
a blade for insertion into a mouth of the patient, the blade being formed into an approximately rectangular plate shape, having a tongue depressor which is bent downwardly in a concave shape, and having on a side edge of the tongue depressor in a downwardly extending manner a pushing plate configured for pushing a tongue toward one side in an oral cavity of the patient;
a grippable handle having a distal end to which the blade is connected,
a first electrode mounted on a distal end portion of the tongue depressor,
a second electrode configured to contact the patient's body in a vicinity of an epiglottis of the patient, and
electrical connections between the first electrode and the second electrode, and
wherein during a power on state of the laryngoscope, a low frequency current is conducted between the first electrode and the second electrode, and
wherein during the power on state, the first electrode is configured to give tetanic stimulation to muscles around the epiglottis, whereby the epiglottis is lifted, exposing the trachea inlet portion so as to facilitate said observation of the trachea inlet portion.

2. The laryngoscope according to claim 1 in combination with a supply of the low frequency current in the form of a pulse current having a frequency of 10 to 100 Hz and an electric current value of 10 mA to 100 mA.

3. The laryngoscope according to claim 1, in which the blade comprises an insulating cover which covers at least the distal end portion of the blade and wherein the first electrode and second electrode are mounted on said insulating cover.

4. The laryngoscope according to claim 1, further comprising an imaging part mounted on the distal end portion of the blade, and a display part tiltably mounted on a proximal end of the handle for displaying an image picked up by the imaging part.

5. A laryngoscope configured to facilitate observation of a trachea inlet portion of a patient, comprising
- a blade for insertion into a mouth of the patient,
- a grippable handle having a distal end to which the blade is connected,
- a first electrode and a second electrode mounted on a distal end portion of the blade, said first electrode and blade being configured so that the first electrode is positioned in contact with muscle around an epiglottis of the patient when the blade is inserted,
- electrical connections between the first electrode and the second electrode though which a low frequency current is conducted between the first electrode and the second electrode, and
- means for electrically facilitating lifting of the epiglottis by which the trachea inlet portion is exposed, so as to facilitate said observation of the trachea inlet portion.

* * * * *